United States Patent
Dixon et al.

(10) Patent No.: US 7,625,411 B2
(45) Date of Patent: Dec. 1, 2009

(54) INSECTICIDALLY TREATED FABRIC HAVING IMPROVED WASH DURABILITY AND INSECTICIDAL EFFICACY AND METHOD FOR ITS PRODUCTION

(75) Inventors: Timothy R. Dixon, Randleman, NC (US); Michael W. Ensley, Eden, NC (US); David M. Wright, Kernersville, NC (US); Michael P. Bralkowski, Lexington, NC (US); Paul D. Weipert, High Point, NC (US); Donna Moser, High Point, NC (US)

(73) Assignee: Piedmont Chemical Industries I, LLC, High Point, NC (US)

( * ) Notice: Subject to any disclaimer, the term of this patent is extended or adjusted under 35 U.S.C. 154(b) by 257 days.

(21) Appl. No.: 10/882,291

(22) Filed: Jul. 2, 2004

(65) Prior Publication Data

US 2006/0000025 A1    Jan. 5, 2006

(51) Int. Cl.
*D06M 13/402*    (2006.01)
(52) U.S. Cl. .................... 8/115.6; 8/115.7; 8/116.1; 252/8.61; 424/405; 424/411; 424/413; 428/365
(58) Field of Classification Search ............... 8/171, 8/470, 501, 526, 582, 648, 115.6, 115.7, 8/116.1; 252/8.6, 301.21, 8.61; 427/158; 424/405, 406, 411, 413; 428/414, 365
See application file for complete search history.

(56) References Cited

U.S. PATENT DOCUMENTS

| | | | | |
|---|---|---|---|---|
| 4,460,374 A * | 7/1984 | Abel et al. | ...................... | 8/501 |
| 4,559,150 A * | 12/1985 | Becker et al. | .................. | 8/648 |
| 5,294,445 A * | 3/1994 | Sieveking et al. | ........... | 424/411 |
| 5,898,960 A * | 5/1999 | Hill | ............................... | 5/120 |
| 6,255,352 B1 * | 7/2001 | Grammenos et al. | ........ | 514/640 |
| 6,322,803 B1 * | 11/2001 | Van Voris et al. | ........... | 424/406 |
| 6,555,228 B2 * | 4/2003 | Guritza | ....................... | 428/414 |
| 6,649,727 B1 * | 11/2003 | Anderson et al. | ............. | 528/71 |
| 2002/0039593 A1 * | 4/2002 | Tucci et al. | ................. | 424/411 |
| 2005/0132500 A1 * | 6/2005 | Karl et al. | .................. | 8/115.51 |

* cited by examiner

*Primary Examiner*—Lorna M Douyon
*Assistant Examiner*—Amina Khan
(74) *Attorney, Agent, or Firm*—Isaac A. Angres

(57) ABSTRACT

The invention provides a method for preparing an insecticidally treated textile having improved properties. A novel combination of an insecticide and certain polymeric binder(s) or dye fixatives is used to coat and/or impregnate fabric via a combination of application methods used in the textile industry. The insecticide-binder or insecticide-dye fixative combination and the method by which it is applied to the textile yield a coated fabric and, ultimately, finished goods with improved wash durability of the insecticide over several launderings and prolonged insecticidal efficacy.

9 Claims, No Drawings

INSECTICIDALLY TREATED FABRIC HAVING IMPROVED WASH DURABILITY AND INSECTICIDAL EFFICACY AND METHOD FOR ITS PRODUCTION

FIELD OF THE INVENTION

The invention pertains to insecticidally treated fabric and methods for its preparation, wherein the method by which, and materials with which the fabric is treated yields a textile of improved wash durability and, consequently, the useful items made from such fabrics demonstrate prolonged and improved insecticidal efficacy.

BACKGROUND OF THE INVENTION

Permethrin, a broad-spectrum insecticide useful against a variety of pests on nut, fruit, vegetable, cotton, ornamental, mushroom, potato, and cereal crops. Permethrin is a synthetic pyrethroid which exhibits repellent as well as knockdown and kill activity against insects. Pyrethroids, including both the naturally-occurring compounds and their synthetically prepared analogs effectively control a variety of pests, such as ticks, cockroaches, houseflies, mosquitoes, black flies, fleas, and other flying or crawling insects. Pyrethroids are not harmful to plants, food, animals or humans, and leave no harmful residues. Permethrin has also been applied on fabric to help combat mosquitoes, ticks, fleas, bedbugs, chiggers, and flies.

Fabrics coated with active agents, and in particular insecticidal agents, are known in the patent literature, as well as compositions and methods for preparing such treated textiles. These fabrics have beneficial utility when sewn into an article of manufacture such as a tent, tarpaulins, sleeping bag, and protective outerwear garments for both civilian and military applications. For example, U.S. Pat. Nos. 3,859,121 (Yeadon et al), 4,765,982 (Ronning et al), 5,089,298 (McNally et al), 5,198,287 (Samson et al), 5,252,387 (Samson et al), 5,503,918 (Samson et al), 5,631,072 (Samson et al), 6,015,570 (Tucci et al), 6,030,697 (Samson et al), and 6,440,438 (Platts) all pertain to textile fabrics that have been treated with an insect repellent.

A major concern of using permethrin as an insect repellent in treated fabrics resides in the wash durability of the insecticide. That is, the retention of permethrin in garments made from treated fabric through repeated wash cycles during machine laundering. It is to this aspect of insecticidally-treated textiles that the present invention pertains.

For example, U.S. Pat. No. 5,089,298 discloses a synergism between an amylopectin (a water soluble form of starch)-permethrin combination on textile fabrics to afford greater retention of permethrin in clothing through repeated wash cycles as compared to garments treated only with permethrin. Another example is disclosed in U.S. Pat. No. 5,503,918 wherein the addition of polyvinyl acetate as a binder for the permethrin dispersion preserves the effectiveness of the permethrin through more washings of the fabric than does the amylopectin used in the '298 patent. U.S. Pat. No. 5,631,072 discloses wash durable permethrin-treated garments prepared from a fabric that is either impregnated or single-side surface-coated with a dispersion of permethrin. In the case of impregnation, a dispersion of permethrin, a polymeric binder such as acrylic copolymer or polyvinylacetate, and optionally a cross-linking agent (e.g., methylated melamine resin), are used. In the single-side surface coating embodiment, the fabric is treated with the insecticide and a thickener (e.g., carboxymethylcellulose), and optionally a polymeric binder that is optionally cross-linked.

Additional patents focusing on one or both of incorporation and retention of either permethrin or a pyrethroid on fabric are as follows:

U.S. Pat. No. 3,859,121 teaches methods for retarding insect repellent contamination of foodstuffs stored in contact with cellulosic textile that has been treated with such repellent, by incorporating into the impregnation composition an antimigrating agent. An insecticidal combination of pyrethrin and piperonyl butoxide are impregnated in association with an emulsifing polyoxyethylene sorbitol ester of a mixed $C_{12}$ fatty acid, a hydroxyalkyl cellulose thickener, and an antimigrating agent such as water soluble polyalkylene glycol, polypropylene triol or pentol of specified average molecular weight, corn oil, tung oil, linseed oil, linoleic acid dimer or trimer, and others.

U.S. Pat. No. 4,765,982 discloses controlled release insect control devices (e.g., webs, tapes, sheets, pads) based on microencapsulated pyrethroid insecticide that self-adheres to rough-surfaced fibers comprised of graft polymers of cellulose and an ethylenically unsaturated material copolymerizable therewith.

U.S. Pat. No. 6,030,697 discloses a method for impregnating BDU's (battle dress uniforms), made from conventional (e.g., untreated twill) fabric with permethrin by adding an aqueous solution (approximately 1%) of permethrin to the wash cycle of an industrial washing machine, and returning all extracted and spin waters containing permethrin to a holding tank for subsequent reuse.

U.S. Pat. No. 5,198,287 discloses a tent fabric with a water repellent and flame retardant coating that includes the insecticide permethrin. The patent focuses on the oxygen- and light-sensitivity of permethrin. According to the '287 invention, permethrin is incorporated in the coating on the inner surface of the tent fabric to shield the permethrin from oxygen and ultraviolet light, thereby providing an effective life of more than six months for the permethrin. Similarly, U.S. Pat. No. 5,252,387 also deals with the oxygen- and light-sensitivity of permethrin in insect repellent fabric and discloses that permethrin can be preserved in the fabric by placing a barrier layer over the permethrin to protect the permethrin from degradation by ultraviolet light and oxygen.

The use of binders in coating "actives" on textiles is widely known in the literature and practiced in the textile industry. More specifically, polymer binders are utilized to aid in improving adhesion and abrasion resistance of the "active" (e.g., a flame retardant, a water repellant, an insect repellant.) U.S. Pat. Nos. 4,594,286 and 4,833,006 are examples of flame resistant, water repellant woven fabrics using blocked polyester/polyether urethane prepolymer or polyfunctional (unblocked) isocyanate, respectively, as binders to aid in the retention of coated "active".

U.S. Pat. Nos. 5,300,192, 5,447,977, 5,571,618, 5,609,727, and 5,611,885 are all commonly assigned to Weyerhaeuser Co. and pertain to the use of reactivatable binders for binding particles to fibers, particularly wet laid or high bulk fibers for web or sheet production, either cellulosic (wood pulp) or synthetic in nature. These patents disclose both polymeric and non-polymeric organic binders having multiple functionalities which, via a combination of hydrogen bonding and coordinate covalent bonding, bind to both the fiber substrate and the particulate to be adhered. Both the fiber and the particulate are functionally reactive with the binder. Examples of polymeric binders include PEG, PPG, polyacrylic acid, polyamides, polyamines, polyaldehydes, and poly(caprolactone) diol. Examples of non-polymeric binders include glycerin, ascorbic acid, urea, glycine, pentaerythritol, a monosaccharide, a disaccharide, citric acid, tartaric acid, dipropylene glycol, and DMDHEU. The binders of the Weyerhaeuser patents have reactivatable funtionality, allowing, e.g., the binder to be adhered to the fiber at one point in production and at a later point in time the functionality for binding the particulate is activated to bind the particulate. While the preferred particles for adhering to the fibrous products or high bulk fibers of most of these patents are superabsorbent particles and/or antimicrobials (e.g., to produce a diaper or other absorbent hygiene product), these patents disclose a long and diverse laundry list of particulates that can be bound to the fibrous products, including, e.g., certain insecticides. (Table I). Permethrin, however, is not recited. Additionally, while the nature of the bonding (i.e., either H-bond or coordinate covalent bond) of the particles to the binder affords the particles to stay in contact with the fibers and resist dislodgement therefrom by mechanical forces applied to the endproduct (a fibrous mat) during manufacture, storage or use, the fibrous products to which these patents pertain are not intended to be laundered, either once or repeatedly. Hence the Weyerhaeuser disclosures do not appreciate the challenges posed by improving the wash durability of garments made from permethrin-treated woven textiles.

SUMMARY OF THE INVENTION

The invention is directed to a method of enhancing the wash durability of insecticidally-treated fabric and consequently and additionally to increasing the efficacy of the same to repel insects before and after repeated machine launderings.

The invention pertains more specifically to a method of impregnating a fabric with a dispersion of an insecticide and a retention additive that is either a binder polymer, a cross-linking agent, or a dye fixative agent, to produce an effective and improved insect repelling fabric.

The invention pertains further to a method of enhancing the wash durability of permethrin-treated fabric and consequently and additionally to increasing the efficacy of such permethrin-treated fabric to repel insects before and after repeated machine launderings by impregnating the fabric with a dispersion of an insecticide and a retention additive that is either a binder polymer, a cross-linking agent, or a dye fixative agent.

The invention provides for permethrin-treated fabrics that are intended for use in garment manufacture wherein the garments made from such fabrics demonstrate the improved wash durability and improved insect repelling efficacy of permethrin contained in the fabric over repeated machine launderings.

The invention pertains further to any finished good, whether a garment or tent or other fabric structure that comes into shielding contact with a subject to be protected from insects, prepared from the improved insect-repelling fabric.

These and other embodiments of the invention will become more evident from the detailed description of the invention that follows.

DETAILED DESCRIPTION OF THE INVENTION

The fabric or textile substrate to be treated in accordance with the invention is not limited as to type. Thus cotton, rayon, linen, polyester, natural and synthetic polyamides ("nylons"), acrylic, cellulose acetate, polyaramide, polypropylene fabric, blends of these, for example, cotton and polyester, cotton and nylon, are suitable fabrics in the context of the invention. Leather, both natural and man-made, are also contemplated as a garment material suitable for insecticidal impregnation according to the invention. In a preferred embodiment of the invention the fabric is a polyester fabric. In another preferred embodiment the fabric is a nylon or a nylon blend.

According to federal government guidelines, the target add-on for permethrin on the fabric is 1.25 grams/meter$^2$, having been determined by the National Research Council that at this level, a soldier wearing permethrin-impregnated BDU for upwards of 18 hours a day, seven days week for several (10) years was unlikely to experience adverse health effects, and that the risk to garment workers handling fabric impregnated at this rate was even less. Before a given fabric can be treated in accordance with the present invention, it is necessary to calculate the proper concentration of insecticide, e.g., permethrin, present in an aqueous impregnating bath such as a pad mix. That calculation is dependent on the following parameters:

A) fabric weight (in grams/M$^2$);
B) target permethrin (in grams/M$^2$)(set at 1.25 g/M$^2$);
C) percent wet pick-up of fabric; and
D) percent available permethrin in the commercial formulation being used (set by the manufacturer of the insecticide).

Parameters 1, 2, and 4 are rather straight forward to determine; the information for determining their respective values is either provided (e.g., by the manufacturer) or is easily ascertained by weighing and measuring the fabric to be treated. For parameter A, the "fabric weight" is typically expressed in the US textile market/industry as "ounces/linear yard"; therefore it will be necessary to convert those units to grams/M$^2$ using standard conversion factors in order to plug the values into the permethrin calculation below. The percent wet pick-up of a given fabric (variable "C") to be insecticidally treated is defined according to the following formula:

$$\frac{\text{Wet Weight} - \text{Dry Weight}}{\text{Dry Weight}} \times 100 = \% \text{ Wet Pick-up of the Fabric,}$$

wherein the dry weight is obtained by weighing a piece of the fabric to be treated and recording its weight, and the wet weight is obtained by soaking the same piece of fabric in water until thoroughly wet, running the soaked fabric through a pad squeeze roll which duplicates production squeeze pressures, reweighing and recording that weight.

The calculation for the quantity of permethrin (expressed as a percentage of the aqueous pad mix) is as follows:

$$\frac{[(B/A) \times (100/C)]}{(D/100)} \times 100 = \% \text{ Permethrin present in the aqueous pad mix,}$$

wherein A, B, C, and D are defined above. The "% permethrin" is of the active only, to clarify from, for example, the commercial preparation (Evercide® Permethrin 40% Manufacturing Concentrate 2778—manufactured by McLaughlin Gormley King Co. in Minneapolis Minn.) which is 40% permethrin in composition. It is a routine calculation to ascertain how much of a commercial insecticidal preparation to add to the aqueous pad mix once the % active is determined from the above formula. Thus for any given type of fabric to be treated in accordance with the method of the invention, the textile worker is able to determine precisely and without undue experimentation, the desired fabric add-on.

For the sake of example only, the following ranges serve as a rough guide for the values of permethrin to be added to the pad bath. The ranges however were determined using the above calculations and based on the following assumptions about the particular fabric to be treated, namely, 1) treating a 60 inch width fabric having 2) 100% wet pick=up. Thus, a fabric with a fabric yield (or weight) of from 1 to 4 ounces per square yard (1-4 oz/yd$^2$) and further characterized by assumptions 1) and 2), would require a pad bath that is from 2 to 9% permethrin based on the weight of the bath size. In another scenario, a fabric with a fabric yield (or weight) of from 5 to 10 ounces per square yard (5-10 oz/yd$^2$) and further characterized by assumptions 1) and 2), would require a pad bath that is from 1 to 2% permethrin based on the weight of the bath size. In another scenario, a fabric with a fabric weight of from 5 to 10 ounces per square yard (5-10 oz/yd$^2$) and further characterized by assumptions 1) and 2), would require a pad bath that is from 1 to 2% permethrin based on the weight of the bath size. For fabrics weighing 11 oz./yd$^2$ or heavier, under the stated assumptions, one would add less than 1% permethrin based on the weight of the bath size. Once again, to satisfy the enablement requirement of the present disclosure, the amount of insecticide to be added to the bath to achieve the desired fabric add-on, is determined based on the properties (weight, width, % wet pick-up) of the fabric, the % available insecticide in the insecticidal formulation, using the stated calculation. The ranges set forth above are merely shown to provide a general idea of how much permethrin formulation (e.g., Evercide®) on a weight percentage basis needs to be added to a pad bath for fabrics of various weights and specified width and pick-up.

The method of incorporating the insecticide into the fabric is by impregnation or by exhaust methods. Thus application by conventional impregnation methods such as dipping, padding or spray processes are within the scope of the invention, as are conventional exhaust processes using one or more of long or short liquor ratios (e.g. liquor-to-goods ratios of from 100:1 to 0.5:1), optimizing (i.e., raising) the temperature of the aqueous bath, and mildly acidifying the bath conditions. In a preferred embodiment of the invention permethrin is impregnated into the fabric substrate by padding, using a pad bath at ambient temperature.

The wash durability of the insecticide impregnated in the fabric is improved by adding a retention additive or polymer binder to the pad mix or bath that also contains the insecticide. The term "retention additive" is used to designate a compound that is not a known polymer binder, but rather a compound with a different function but that in the context of the invention, is effective to improve the wash durability of the insecticide. Depending upon the type of fabric to be insecticidally treated, the type of additive or binder varies in accordance with the invention. As previously stated, fabrics such as cotton, rayon, linen, polyester, natural and synthetic polyamides ("nylons"), acrylic, cellulose acetate, polyaramide, polypropylene fabric, and blends of these (e.g., cotton and polyester, cotton and nylon) are suitable for treatment in accordance with the invention. Particularly preferred fabrics are polyester and woven nylons.

In the case of nylon fabrics, the additive that improves the wash durability of the permethrin is either a water-soluble nylon-based polymer, a polyurethane binder or a dye fixative agent. Water-soluble, nylon-based polymers suitable in the practice of the invention are typically referred to as polyetheramide polymers. These polymers arose as an improvement to traditional nylon polymers, e.g., by replacing the alkylene diamine reactant (typically reacted with a dicarboxylic acid such as adipic acid as in the formation of nylon 6,6) with an alkylene glycol diamine. In general, polyetheramide polymers can be formed by reacting polycarboxylic acids with polyetheramines. Alternatively, these polymers can be formed by copolymerizing caprolactam with, e.g., polyethyleneoxy diamines and a dibasic acid such as terephthalic acid. Polyetheramide polymers and block polymers and methods for their preparation are known in the art. See, for example, U.S. Pat. Nos. 3,454,534, 4,919,997, 5,166,309 (block polyetheramides), and 5,342,918 (carboxyl-terminated polyetheramides); French Patent Publication Nos. 2,273,021, 2,384,810, and 2,401,947; German publication DE 3,428,405 discloses polyetheramides prepared from a stoichiometric mixture of oligoamidediacid and of oligoetherdiol, and from 3-30% relative to the mixture of diol of low molecular weight; Japanese publications J63-048,332, J63-227,238, J63-280,736, J63-105,032, and J63-182,343 describe block polyetheramides and processes for their preparation. More particularly, suitable polyetheramide polymers in the practice of the invention include copolymers of a polyalkyleneglycol and a poly($C_3$-$C_{12}$)alkyllactam. In a more preferred embodiment of the invention, copolymers of PEG/polycaprolactam polymer and PEG/polylauryllactam polymer are employed to bring about the improved wash durability of the insecticidally treated fabric.

The polyurethane binder of the invention is typically a polyurethane dispersion. The term polyurethane dispersion as used herein describes stable mixtures of polyurethane polymers in water. Methods of preparing polyurethane dispersions are well known in the art and many of polyurethane dispersions are commercially available. Polyurethane polymers are generally characterized by their monomer content and most commonly involve the reaction of a diisocyanate with a polyol and chain extender. While the present inventors believe the polyurethane dispersion can be a stable aqueous mixture of any known polyurethane, typically the polyurethanes suitable for the use in the aqueous polyurethane dispersions are the reaction products (a) an isocyanate compound having at least two isocyanate (—NCO) functionalities per molecule; (b) a polyol having at least two hydroxy functionalities per molecule and a molecular weight ranging from 250 to 10,000 g/mole. The polyol may be selected from those commonly found in polyurethane manufacturing such as hydroxy-containing or terminated polyethers, polyesters, polycarbonates, polycaprolactones, polythioethers, polyetheresters, polyolefins, and polydienes. Suitable polyether polyols for the preparation of polyether polyurethanes and their dispersions include the polymerization products of cyclic oxides such as ethylene oxide, propylene oxide, tetrahydrofuran, or mixtures thereof. Polyether polyols commonly found include polyoxyethylene (PEO) polyols, plyoxypropylene (PPO) polyols, polyoxytetramethylene (PTMO) polyols, and polyols derived from the mixture of cyclic oxides such as poly(oxyethylene-co-polypropylene) polyols. Typical molecular weight of polyether polyols can range from 250 to 10,000 g/mole. Suitable polyester polyols for the preparation of polyester polyurethanes and their aqueous dispersions include; hydroxy-terminated or containing reaction products of ethylene glycol, propylene glycol, diethylene glycol, neopentyl glycol, 1-4, butanediol, furan dimethanol, polyether diols, or mixtures thereof, with dicarboxylic acids or their ester-forming derivatives.

Modified polyether polyurethanes such as polyetherester polyurethanes and polyethercarbonate polyurethanes may also be suitable polyurethanes for the preparation of aqueous polyurethane dispersions. These modified polyether polyurethanes can be derived by incorporating additional polyester polyols or polycarbonate polyols into polyether polyols during the polyurethane manufacturing.

Typically the polyurethane polymer useful to prepare the polyurethane dispersion as component in the compositions of the present invention is selected from polyether polyurethanes, polyester polyurethanes, polycarbonate polyurethanes, polyetherester polyurethanes, polyethercarbonate polyurethanes, polycaprolactone polyurethanes, hydrocarbon polyurethanes, aliphatic polyurethanes, aromatic polyurethanes, and combinations thereof.

Polyurethane dispersion as used herein encompasses both conventional emulsions of polyurethane polymers, for example where a preformed polyurethane polymer is emulsified into an aqueous medium with the addition of surfactants and application of shear, and also includes stable mixtures of self-dispersing polyurethane polymers. Polyurethane dispersions of self-dispersing polyurethane polymers are well known in the art and many are commercially available. These polyurethane dispersions are generally free of external surfactants because chemical moieties having surfactant like characteristics have been incorporated into the polyurethane polymer and therefore are "self emulsifying" or "self dispersing". Representative examples of internal emulsifier moieties that can be incorporated into the polyurethane dispersions useful in the present invention include; ionic groups such as sulfontates, carboxylates, and quaternary amines; as well as nonionic emulsifier groups such as polyethers. Such polyurethane dispersions are well known in the art, and are typically prepared by either a one stage or two-stage process. Typically, a isocyanate-terminated polyurethane prepolymer is made from isocyanates, polyols, optional chain extender, and at least one monomer containing a hydrophilic group to render the prepolymer water dispersible. The polyurethane dispersion can then be prepared by dispersing the isocyanate-terminated polyurethane prepolymer in water with other polyisocyanates. Further chain extension can be affected by the addition of chain extenders to the aqueous dispersion. Depending on the choice of the hydrophilic group used to render the polyurethane polymer water dispersible, an additional reaction step may be needed to convert the hydrophilic group to an ionic species, for example converting a carboxyl group to an ionic salt or an amine to an amine salt or cationic quaternary group.

Representative, non-limiting examples of polyurethane dispersions that are suitable for use as the binder component in the compositions of the present invention, as well as general descriptions of techniques useful to prepare polyurethane dispersions can be found in U.S. Pat. Nos. 4,829,122, 4,921, 842, 5,025,064, 5,055,516, 5,308,914, 5,334,690, 5,342,915, 5,717,024 5,733,967, 6,017,998, 6,077,611, 6,147,155, and 6,239,213.

Representative, non-limiting examples of commercially available polyurethane dispersions that are suitable for use as component (B) in the compositions of the present invention include: WITCOBOND W 290H, W-290H, W-296, and W213 (Uniroyal Chemical Division, Crompton Corporation, Middlebury, Conn.); DISPERCOLL U42, BAYHYDROL 121, and Bayhydrol 123 polycarbonate polyurethane dispersions (100 Bayer Road, Pittsburgh, Pa. 15025); SANCURE 2710 and 2715 aliphatic polyether polyurethane dispersions (Noveon, Inc. Cleveland, Ohio); NEOREZ R-966, R-967, R-9603 aliphatic polyurethane dispersions (NeoResins Division, Avecia, Wilmington, Mass.).

Alternatively, for nylon fabrics the additive may also be a dye fixative agent. Without being bound by any one particular theory of the mechanism of interaction and the improved results obtained from using a dye fixative agent in association with permethrin, it is thought that permethrin will "bond" with the fixative into the fabric and make it more durable to home laundering. The dye fixing agent can be any of a variety of fixing agents known for application to polyamide fiber to improve dye washfastness. These agents are typically compounds or low molecular weight polymers with anionic groups which can associate with the nitrogen-containing groups of the polyamide polymer and form a surface layer that reduces diffusion of the dye out of the treated fiber. "Syntan" is usually used to describe the class of synthetic fixing agent including condensation products of aromatic sulfonic acids and formaldehyde that are in common usage in the industry for acid dye fixation on nylon. Syntans and their derivatives include sulfonated napthol-formaldehyde condensation products; sulfonated phenol-formaldehyde condensation products; polymers of methylacrylic acid or its alkali metal salt, and up to 70 weight percent of one or more monomers having ethylenic unsaturation and containing 2 to 20 atoms; a polymer of maleic acid or fumaric acid, or alkali metal salts thereof, and up to 70 weight percent of an ethylenically unsaturated aromatic comonomer containing 2 to 20 atoms; polymers of alpha-substituted acrylic acids or esters polymerized in the presence of a sulfonated aromatic formaldehyde condensation polymer; and polymers of a sulfonated hydroxyaromatic ester of an alpha-substituted acrylic acid or acrylic acid. Syntans are commercially available and are sold, for example, under the trademarks ERIONAL® (Ciba-Geigy Corp, Greensboro, N.C.), INTRATEX® (Crompton & Knowles Corp., Stamford, Conn.), MESITOL® (Mobay Corp. Pittsburgh, Pa.), and NYLOFIXAN® (Sandoz Chemical Corp., Charlotte, N.C.). The preferred dye fixing agents in the practice of the invention are sulfonated naphthalene formaldehyde condensates, sulfonated phenol formaldehyde condensates, dihydroxy diphenyl sulfone formaldehyde condensates, and mixtures thereof.

In the case of insecticidally treating a polyester fabric, the retention additive is a polymeric binder. More particularly, the polymeric binder is a polyester polymer or resin. The use of polyester (co)polymers for treating fibers, including polyester fibers and fabrics, is known in the art. The following patent disclosures exemplify such polymers and uses: U.S. Pat. Nos. 3,712,873, 3,893,929, 3,959,230, 3,962,152, 4,027, 346, 4,125,370, and 4,370,143. In one or more embodiments of the invention, the polyester polymer is preferably comprised of a reaction product of a polyalkyleneglycol, an aromatic dicarboxylic acid, and a glycol. The polyalkylene glycol component of the polyester may be those normally having an average molecular weight in the range of 600-12,000, preferably in the range of 1,000-5,000, and may include polyethylene glycol, polyethylene glycol-polypropylene glycol copolymer, polyethylene glycol-polytetramethylene glycol copolymer, polypropylene glycol and polyhydric alcohol-ethylene oxide adduct etc. Other examples of usable alkylene glycols are monophenylethers, monoethylethers and monomethylethers of polyethylene glycol and polypropylene glycol.

The dicarboxylic acid component has the following general formula HOOC-A-COOH, wherein A is a bivalent organic radical selected from the group consisting of alkylene, arylene, aralkylene, alkarylene and cycloalkylene radicals having from 3 to about 14 carbon atoms. Preferably, the dibasic carboxylic acid is an aromatic dicarboxylic acid.

The glycol component is a compound having the following general formula HO—X—OH, wherein X is a bivalent organic radical selected from the group consisting of alkylene and cycloalkylene radicals having from 2 to about 4 carbon atoms. When X is alkylene, examples of suitable radicals are ethylene, propylene and butylene, and when X is a cycloalkylene radical, examples of suitable radicals are cyclopropylene and cyclobutylene.

Representative polyesters suitable in the practice of the invention include terephthalic acid-alkylene glycol-polyalkylene glycol, terephthalic acid-isophthalic acid-alkylene glycol-polyalkylene glycol, terephthalic acid-alkylene glycol-polyalkylene glycol monoether, terephthalic acid-isophthalic acid-alkylene glycol-polyalkylene glycol monoether. More preferably, the polyester polymer comprises a poly($C_2$-$C_4$)alkyleneterephthalate (e.g., polyethyleneterephthalate or polytetramethylene-terephthalate) or mixtures thereof. An example of suitable polyester polymer is a proprietary material available under the tradename Pomoco253 (a product of Piedmont Chemical Industries I, LLC in High Point, N.C.) which is a polyester derived from terephthalic acid and glycols. Another suitable polyester polymer is the next generation of Pomoco 253, named Pomoco 253-P and also available from Piedmont Chemical Industries I, LLC in High Point, N.C.

For fabric blends of polyester and cotton, or even fabrics that are entirely cellulosic, the present inventors have found that an effective polymeric binder system for the permethrin may also be crosslinking agent. Crosslinking agents are widely used in the textile industry in the dyeing of certain fabric types (e.g., cellulosics) or to impart desirable properties to the textile (e.g., wrinkle recovery or crease resistance, tensile strength, and fabric smoothness). For example, the disclosures of U.S. Pat. Nos. 4,629,470 and 5,298,584 pertain to cellulosic substrates intended for eventual dyeing and which are pre-treated with finishes in order to render the fabric surface more receptive to dyes and to improve color strength of the dyed product. Such finishes comprise as major components a crosslinking agent, a catalyst and other reactive additives such as glycols or choline chloride that graft to the crosslinking agent. U.S. Pat. No. 4,396,391 provides a crosslinking agent for use as a crease-resistant finish for cellulose-containing textiles, which crosslinking agent is a reaction product of dimethylol dihyroxyethylene urea (DMDHEU) or an alkylated DMDHEU with a polyol. Crosslinking agents useful in the present invention are those which preferably possess multiple reactive sites. These include, for example, dimethylol urea, partially methylolated urea, dimethylol ethyleneurea, dimethylol propyleneurea, dimethylol dihydroxyethyleneurea (DMDHEU), alkylated DMDHEU, trimethylol acetylenediureine (3ACD), tetramethylol acetylenediureine (4ACD), and methylol melamine (TMM), dimethylol propyl carbamate, and forms of these that have been modified by grafting, e.g., with polyalkylene glycols of suitable molecular weight. In a preferred embodiment of the invention, a DMDHEU/PEG modified crosslinking agent is effective in enhancing the wash durability of permethrin-treated cotton and cotton/polyester blend fabrics.

Depending on the fabric being insecticidally treated, the polymer binder, crosslinking agent or dye fixing agent, is added to the same bath to which the permethrin (or other insecticide) is also added. The binder, crosslinker or dye fixative is present in the pad bath in an amount that varies widely from 0.01 to 20% by weight of the bath size; the wide range specified is reflective of the fact that the amount of binder, crosslinking agent or dye fixative necessary will be dependent upon the wet pick-up of the fabric. Generally a fabric with a higher wet pick-up value will require a smaller amount of binder, crosslinker or dye fixative in the pad bath, and a fabric with a lower wet pick-up value will require a larger amount. Thus, the amount of "the additive" needed depends on the type of fabric being treated (e.g., nylon, polyester, cotton, acrylic) and the relevant textile properties thereof (i.e., at least the wet pick-up of the fabric). More preferably the binder, crosslinker or dye fixative is present from about 0.5 to 10% by weight of the bath size, and in a preferred embodiment "the additive" is present from about 1 to 3% by weight of the bath size. What is essential about the amount of additive used is that it be the least amount necessary to achieve the enhanced durability of the insecticide without being detrimental to the desired hand, or feel, of the fabric.

In a less preferred and alternate embodiment, the fabric can be treated sequentially, rather than the preferred method of padding the fabric in a single pad bath that contains both the retention additive and the permethrin. Thus, for example, the fabric can be treated or padded with the polymeric binder, crosslinking agent or dye fixative agent at one point in time at one location, and then be padded with insecticide at a later point in time, and possibly at a different location, provided that the interim time and conditions to which the fabric is exposed (between the first pad and the second pad) do not have a significant adverse affect on the binding of insecticide to the fabric and the level of enhanced wash durability achieved herein.

Following impregnation, the fabric is typically subjected to at least one after-treatment conventional in textile processing. For example, the insecticidally treated fabric can be subjected to drying or curing following the padding or exhaust application. Additionally the fabric may be after-treated with customary finishes to improve, e.g., the hand, water repellancy, wrinkle resistance, brightness, antibacterial nature of the textile, provided that none of these additional agents interfere with either the extended wash durability or the insecticidal efficacy.

EXAMPLE

The following examples are provided solely to illustrate the invention, and not to limit the scope of the invention to the particular fabrics, polymeric binders and/or dye fixative agents used therein.

A polyester warp fleece weighing approximately 7.6 oz. per linear yard was used in this trial. Based on the weight of the fabric, calculating the percent wet pick-up the of fabric using production sqeeze pressures in the pad application, and the amount of permethrin target (1.25 $g/m^2$), the quantity of permethrin to be added to the pad bath was calculated using the above equation to be 1.68%. Also added to the pad bath was a polyester-based binder system (Pomoco 253P) at 2.50% based on the weight of the bath. The fabric was padded and dried at a normal drying temperature for polyester (330 to 350° F.).

After the application of permethrin to the fabric, samples of the treated fabric were extracted with toluene according to the procedure outlined below in order to determine the amount of permethrin loaded onto the fabric. A swatch of fabric measuring approximately two feet by two feet is cut from the treated roll of fabric. From that swatch, 3 smaller pieces measuring 10 cm by 10 cm, were cut and used for extraction of permethrin. Each 10 by 10 swatch was placed in a 250 ml flat-bottomed flask, and from 50-75 ml of an extraction solvent (e.g., 1,1,1-trichloroethane) was added thereto. The flask was then equipped with a reflux condenser and placed on a hot plate and allowed to reflux for 0.5-0.75 hr. Once the samples have finished refluxing and have cooled, 0.05mg/ml of dioctylphthalate ("DOP") is added to the liquid fraction as an internal standard for gas chromatography ("gc"). Known standard solutions of permethrin and DOP are prepared for comparison to what has been extracted from the swatches. The calculation used in conducting the gc analysis is as follows:

$$\frac{\text{Area of } cis \text{ and } trans \text{ permethrin}}{\text{Area of dioctylphthalate}} \times \frac{\text{Weight ratio of internal standard}}{\text{Area ratio of internal standard}} \times$$

$$5.006(.955)/10 = \text{permethrin in grams/m}^2.$$

Next, 10×10 inch swatches of the treated fabric were subjected to one or more machine launderings in a laundrometer using the accelerated laundering test (Test Method 61-1996) specified by the AATCC, in order to determine how well the permethrin remained impregnated in the fabric after the washings. After each of the designated washing cycles each swatch of fabric was extracted following the procedure described above in order to determine the amount of permethrin remaining therein. The results are shown in the following table:

| Laundering Conditions | Amount of Permethrin in Fabric (g/m²)/% Remaining | |
| --- | --- | --- |
| permethrin-treated polyester fabric using a binder according to the invention, pre-laundering | 1.11 | |
| after 1 machine laundering | 1.03 | 93% |
| after 3 machine launderings | 1.08 | 97% |
| after 10 machine launderings | 1.02 | 92% |

The results clearly show that initial load of permethrin is impressively retained (92-97%) in the fabric in the presence of the binder according to the invention, even after 10 machine washings. Without incorporation of the binder system of the invention, permethrin washes out of the fabric at nearly 60-80% of the initial amount loaded just after the first wash (e.g., 0.20-0.30 g/m² or less of permethrin remaining); not surprisingly, the amount remaining diminishes rapidly with successive launderings.

In another test run on a polyester fabric treated with Pomoco 253-P, impregnated with permethrin, and subjected to repeated launderings and extractions using procedure similar to that described in the above Example, permethrin was retained at 90% of the initial load after 50 launderings.

Additional durability Testing (For testing purposes only) (Type of fabric: Polyester) were done and the results are as follows:

| (TEST 1) | |
| --- | --- |
| Initial Permethrin amount: | 1.48 g/m2 (Testing purposes only) |
| After 25 washings: | 1.35 g/m2 |
| After 50 washings: | 1.27 g/m2 |
| (TEST 2) | |
| Initial Permethrin amount: | 1.38 g/m2 (Testing purposes only) |
| After 25 washings: | 1.20 g/m2 |
| After 50 washings: | 1.15 g/m2 |
| (TEST 3) | |
| Initial Permethrin amount: | .54 g/m2 (Testing purposes only) |
| After 50 washings: | .50 g/m2 |

The fabrics of the invention were also tested against deer ticks and mosquitoes and the efficacy is in no way hindered by the binder in the permethrin applications. These tests were conducted on both nylon and polyester fabric.

Nylon fabrics were also evaluated using a polyurethane binder known as (Polyester Polyol Aliphatic Isocyanate Urethane Dispersion) Two products were used from Crompton Corp., Witcobond Dispersions Group in Tarrytown, N.Y. (Witcobond W-296 Latex and Witcobond W-290HSC).

The polyurethane binders of the invention also provide for highly effective permethrin retention.

A nylon cordura fabric was treated with the permethrin and polyurethane binder using the procedures described above for the polyester fabrics and the following results were obtained:

| Original Permethrin Values: | One Wash | After 50 washings |
| --- | --- | --- |
| 1.0 grams/m2 (Witcobond W-290HSC) | 1.0 g/m2 | .90 g/m2 (Began from original fabric) |
| .94 grams/m2 (Witcobond W-296 Latex) | .87 g/m2 | .95 g/m2 (Began from original fabric) |

While the invention has been specifically illustrated and described in connection with numerous embodiments and further defined in the appended claims, modifications to the various embodiments are within the spirit and scope of the present invention and will be readily apparent to those of skill in the art.

What we claim is:

1. A method of enhancing the efficacy of nylon fabrics, polyester fabrics and cotton-polyester fabrics to repel insects before and after repeated launderings of said fabrics, said method comprising:
    a) providing a retention additive comprising a solution containing a polyester polyol aliphatic isocyanate urethane binder dispersion of permethrin insecticide; and
    b) impregnating said fabric with said retention additive solution by pad application, wherein the resulting fabric retains said permethrin insecticide at 90% of the initial load after 50 launderings.

2. The method according to claim 1, wherein said solution further includes a dye fixative agent.

3. The method according to claim 2 wherein said dye fixative agent comprises a sulfonated naphthalene formaldehyde condensate, a sulfonated phenol formaldehyde condensate, a dihydroxy diphenyl sulfone formaldehyde condensate, or mixtures thereof.

4. An insect repelling fabric intended for garment manufacture and incorporating an insect repelling effective amount of permethrin and a retention additive for retaining an effective insecticidal amount of permethrin in said fabric following multiple wash cycles of garments made from said fabric, wherein said fabric is selected from the group consisting of nylon fabrics, polyester fabrics and cotton-polyester fabrics, wherein said retention aid comprises a polyester polyol aliphatic isocyanate urethane binder system and wherein said fabric retains said permethrin at 90% of the initial load after 50 launderings.

5. The fabric according to claim 4 wherein the effective insecticidal amount of permethrin is achieved at an application rate of 1.25 g/m² and said retention additive enables retention of permethrin in the fabric following successive machine launderings at levels from 90% to about 95% of said application rate.

6. The fabric according to claim 5 which is machine laundered from 5 to about 50 times.

7. A method of enhancing the efficacy of nylon fabrics, polyester fabrics and cotton-polyester fabrics to repel insects before and after repeated launderings of said fabric, said method comprising a) providing a solution containing a dispersion of permethrin and a polyester polyol aliphatic isocyanate urethane retention additive; and b) impregnating a fabric with said retention additive solution to achieve a permethrin application rate of 1.25 g/m² either by pad application or exhaustion application and wherein said fabric retains said permethrin at 90% of the initial load after 50 launderings.

8. The method of claim 7 wherein said fabric is a nylon fabric.

9. The method of claim 8 wherein said nylon fabric is a cordura nylon fabric.

* * * * *